(12) United States Patent
Vardi et al.

(10) Patent No.: US 8,617,231 B2
(45) Date of Patent: Dec. 31, 2013

(54) DUAL GUIDEWIRE EXCHANGE CATHETER SYSTEM

(75) Inventors: Gil M. Vardi, Town and Country, MO (US); Eric Williams, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1505 days.

(21) Appl. No.: 10/670,168

(22) Filed: Sep. 25, 2003

(65) Prior Publication Data

US 2004/0153136 A1    Aug. 5, 2004

Related U.S. Application Data

(60) Provisional application No. 60/413,552, filed on Sep. 26, 2002.

(51) Int. Cl.
    *A61F 2/84*              (2006.01)

(52) U.S. Cl.
    USPC ........................................ 623/1.11; 623/1.35

(58) Field of Classification Search
    USPC ............... 623/1.11, 1.35, 1.12; 606/108, 194, 606/198; 604/103.04, 1.35
    See application file for complete search history.

(56) References Cited

U.S. PATENT DOCUMENTS

| | | | |
|---|---|---|---|
| 1,598,754 A | 8/1926 | Moschelle | |
| 3,657,744 A | 4/1972 | Ersek | |
| 3,872,893 A | 3/1975 | Roberts | |
| 4,140,126 A | 2/1979 | Choudhury | |
| 4,309,994 A | 1/1982 | Grunwald | |
| 4,410,476 A | 10/1983 | Redding et al. | |
| 4,413,989 A | 11/1983 | Schjeldahl | |
| 4,421,810 A | 12/1983 | Rasmussen | |
| 4,453,545 A | 6/1984 | Inoue | |
| 4,503,569 A | 3/1985 | Dotter | |
| 4,552,554 A | 11/1985 | Gould et al. | |
| 4,681,570 A | 7/1987 | Dalton | |
| 4,689,174 A | 8/1987 | Lupke | |
| 4,731,055 A | 3/1988 | Melinyshyn et al. | |
| 4,733,665 A | 3/1988 | Palmaz | |
| 4,739,762 A | 4/1988 | Palmaz | |

(Continued)

FOREIGN PATENT DOCUMENTS

| | | |
|---|---|---|
| CA | 2318314 | 7/1999 |
| DE | 9014845.2 | 2/1991 |

(Continued)

OTHER PUBLICATIONS

Serruys et al., *The New England Journal of Medicine*, vol. 331, No. 8, pp. 489-495 (1994).

(Continued)

*Primary Examiner* — Elizabeth Houston
(74) *Attorney, Agent, or Firm* — Seager, Tufte & Wickhem LLC

(57) ABSTRACT

A dual guidewire exchange catheter system and methods are provided herein. The dual guidewire exchange catheter system includes two lumens for receiving therethrough a main vessel guidewire and a branch vessel guidewire, respectively. The catheter includes an exit port for each guidewire, at least one of which is a shorter distance from the distal end of the catheter system than the distance from the distal end to the proximal end of the catheter. This allows for management of relatively short guidewire lengths outside the body.

17 Claims, 14 Drawing Sheets

(56) References Cited

U.S. PATENT DOCUMENTS

| | | |
|---|---|---|
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,946,464 A | 8/1990 | Pevsner |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A * | 6/1994 | Sahota ............... 604/101.01 |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Ansel et al. |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jiminez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Anderson |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne et al. |
| 5,693,084 A | 12/1997 | Chutter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon |
| 5,709,713 A | 1/1998 | Evans et al. |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,743,875 A * | 4/1998 | Sirhan et al. ............... 604/96.01 |
| 5,746,766 A | 5/1998 | Edoga |
| 5,749,825 A * | 5/1998 | Fischell et al. ............... 600/3 |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,800,450 A | 9/1998 | Lary et al. |
| 5,800,508 A | 9/1998 | Goicoechea et al. |
| 5,814,061 A | 9/1998 | Osborne et al. |

(56) References Cited

U.S. PATENT DOCUMENTS

| | | | |
|---|---|---|---|
| 5,817,126 A | 10/1998 | Imran | |
| 5,824,008 A | 10/1998 | Bolduc et al. | |
| 5,824,036 A | 10/1998 | Lauterjung | |
| 5,824,040 A | 10/1998 | Cox et al. | |
| 5,824,041 A | 10/1998 | Lenker et al. | |
| 5,824,044 A | 10/1998 | Quiachon et al. | |
| 5,827,320 A | 10/1998 | Richter et al. | |
| 5,833,650 A | 11/1998 | Imran | |
| 5,836,966 A | 11/1998 | St. Germain | |
| 5,837,008 A | 11/1998 | Berg et al. | |
| 5,843,031 A | 12/1998 | Hermann et al. | |
| 5,843,160 A | 12/1998 | Rhodes | |
| 5,843,164 A | 12/1998 | Frantzen et al. | |
| 5,846,204 A | 12/1998 | Solomon | |
| 5,851,210 A | 12/1998 | Torossian | |
| 5,851,464 A | 12/1998 | Davila et al. | |
| 5,855,600 A | 1/1999 | Alt | |
| 5,855,601 A | 1/1999 | Bessler et al. | |
| 5,865,178 A | 2/1999 | Yock | |
| 5,868,777 A | 2/1999 | Lam | |
| 5,871,536 A | 2/1999 | Lazarus | |
| 5,871,537 A | 2/1999 | Holman et al. | |
| 5,891,133 A | 4/1999 | Murphy-Chutorian | |
| 5,897,588 A | 4/1999 | Hull et al. | |
| 5,906,640 A | 5/1999 | Penn et al. | |
| 5,907,893 A | 6/1999 | Zadno-Azizi et al. | |
| 5,913,895 A | 6/1999 | Burpee et al. | |
| 5,913,897 A | 6/1999 | Corso, Jr. et al. | |
| 5,921,958 A | 7/1999 | Ressemann et al. | |
| 5,922,020 A | 7/1999 | Klein et al. | |
| 5,928,248 A | 7/1999 | Acker | |
| 5,938,682 A | 8/1999 | Hojeibane | |
| 5,938,696 A | 8/1999 | Goicoechea et al. | |
| 5,948,016 A | 9/1999 | Jang | |
| 5,951,599 A | 9/1999 | McCrory | |
| 5,961,548 A | 10/1999 | Shmulewitz | |
| 5,967,986 A | 10/1999 | Cimochowski et al. | |
| 5,972,018 A | 10/1999 | Israel et al. | |
| 6,007,517 A | 12/1999 | Anderson | |
| 6,013,054 A | 1/2000 | Juin Yan | |
| 6,013,091 A | 1/2000 | Ley et al. | |
| 6,017,324 A | 1/2000 | Tu et al. | |
| 6,017,363 A | 1/2000 | Hojeibane | |
| 6,024,763 A | 2/2000 | Lenker et al. | |
| 6,030,414 A | 2/2000 | Taheri | |
| 6,033,434 A | 3/2000 | Borghi | |
| 6,033,435 A | 3/2000 | Penn et al. | |
| 6,036,682 A | 3/2000 | Lange et al. | |
| 6,039,749 A | 3/2000 | Marin et al. | |
| 6,042,597 A | 3/2000 | Kveen et al. | |
| 6,045,557 A | 4/2000 | White et al. | |
| 6,048,361 A * | 4/2000 | Von Oepen | 623/1.11 |
| 6,056,775 A | 5/2000 | Borghi et al. | |
| 6,059,823 A | 5/2000 | Holman et al. | |
| 6,059,824 A | 5/2000 | Taheri | |
| 6,066,168 A | 5/2000 | Lau et al. | |
| 6,068,655 A | 5/2000 | Sequin et al. | |
| 6,071,285 A | 6/2000 | Lashinski et al. | |
| 6,086,611 A | 7/2000 | Duffy et al. | |
| 6,090,127 A | 7/2000 | Globerman | |
| 6,090,128 A | 7/2000 | Douglas | |
| 6,096,073 A | 8/2000 | Webster et al. | |
| 6,099,497 A * | 8/2000 | Adams et al. | 604/96.01 |
| 6,117,117 A | 9/2000 | Mauch | |
| 6,117,156 A | 9/2000 | Richter et al. | |
| 6,126,685 A | 10/2000 | Lenker et al. | |
| 6,129,738 A | 10/2000 | Lashinski et al. | |
| 6,129,754 A | 10/2000 | Kanesaka et al. | |
| 6,142,973 A | 11/2000 | Carleton et al. | |
| 6,152,945 A | 11/2000 | Bachinski et al. | |
| 6,165,195 A * | 12/2000 | Wilson et al. | 606/194 |
| 6,165,197 A | 12/2000 | Yock | |
| 6,165,214 A | 12/2000 | Lazarus | |
| 6,179,867 B1 | 1/2001 | Cox | |
| 6,183,506 B1 | 2/2001 | Penn et al. | |
| 6,183,509 B1 | 2/2001 | Dibie | |
| 6,190,403 B1 | 2/2001 | Fischell et al. | |
| 6,193,746 B1 | 2/2001 | Strecker | |
| 6,203,569 B1 | 3/2001 | Wijay | |
| 6,210,380 B1 | 4/2001 | Mauch | |
| 6,210,429 B1 | 4/2001 | Vardi | |
| 6,217,527 B1 | 4/2001 | Selmon et al. | |
| 6,217,608 B1 | 4/2001 | Penn et al. | |
| 6,221,080 B1 | 4/2001 | Power | |
| 6,221,090 B1 | 4/2001 | Wilson | |
| 6,221,098 B1 | 4/2001 | Wilson et al. | |
| 6,231,563 B1 | 5/2001 | White et al. | |
| 6,231,598 B1 | 5/2001 | Berry et al. | |
| 6,231,600 B1 | 5/2001 | Zhong | |
| 6,235,051 B1 | 5/2001 | Murphy | |
| 6,241,762 B1 | 6/2001 | Shanley | |
| 6,258,073 B1 | 7/2001 | Mauch | |
| 6,258,099 B1 | 7/2001 | Mareiro et al. | |
| 6,258,116 B1 * | 7/2001 | Hojeibane | 623/1.16 |
| 6,258,121 B1 | 7/2001 | Yang et al. | |
| 6,261,273 B1 | 7/2001 | Ruiz | |
| 6,261,305 B1 | 7/2001 | Marotta et al. | |
| 6,261,319 B1 | 7/2001 | Kveen et al. | |
| 6,264,682 B1 | 7/2001 | Wilson et al. | |
| 6,273,879 B1 * | 8/2001 | Keith et al. | 604/523 |
| 6,273,911 B1 | 8/2001 | Cox et al. | |
| 6,273,913 B1 | 8/2001 | Wright et al. | |
| 6,287,314 B1 | 9/2001 | Lee et al. | |
| 6,290,673 B1 | 9/2001 | Shanley | |
| 6,293,967 B1 | 9/2001 | Shanley | |
| 6,299,634 B1 | 10/2001 | Bergeron | |
| 6,302,906 B1 | 10/2001 | Goicoechea et al. | |
| 6,309,412 B1 | 10/2001 | Lau et al. | |
| 6,309,414 B1 | 10/2001 | Rolando et al. | |
| 6,312,459 B1 | 11/2001 | Huang et al. | |
| 6,325,821 B1 | 12/2001 | Gaschino et al. | |
| 6,325,826 B1 | 12/2001 | Vardi et al. | |
| 6,334,870 B1 | 1/2002 | Ehr et al. | |
| 6,346,089 B1 | 2/2002 | Dibie | |
| 6,350,278 B1 | 2/2002 | Lenker et al. | |
| 6,355,060 B1 | 3/2002 | Lenker et al. | |
| 6,361,544 B1 | 3/2002 | Wilson et al. | |
| 6,361,555 B1 * | 3/2002 | Wilson | 623/1.11 |
| 6,383,215 B1 | 5/2002 | Sass | |
| 6,387,120 B2 | 5/2002 | Wilson et al. | |
| 6,395,018 B1 | 5/2002 | Castaneda | |
| 6,398,792 B1 | 6/2002 | O'Connor | |
| 6,398,804 B1 | 6/2002 | Spielberg | |
| 6,428,570 B1 | 8/2002 | Globerman | |
| 6,432,133 B1 | 8/2002 | Lau et al. | |
| 6,436,104 B2 | 8/2002 | Hojeibane | |
| 6,436,134 B2 | 8/2002 | Richter et al. | |
| 6,478,816 B1 | 11/2002 | Kveen et al. | |
| 6,482,211 B1 * | 11/2002 | Choi | 606/108 |
| 6,485,511 B2 | 11/2002 | Lau et al. | |
| 6,494,905 B1 | 12/2002 | Zedler et al. | |
| 6,511,504 B1 | 1/2003 | Lau et al. | |
| 6,511,505 B2 | 1/2003 | Cox et al. | |
| 6,520,988 B1 * | 2/2003 | Colombo et al. | 623/1.35 |
| 6,527,799 B2 | 3/2003 | Shanley | |
| 6,540,719 B2 | 4/2003 | Bigus et al. | |
| 6,540,779 B2 | 4/2003 | Richter et al. | |
| 6,572,647 B1 | 6/2003 | Supper | |
| 6,579,309 B1 | 6/2003 | Loos et al. | |
| 6,579,312 B2 | 6/2003 | Wilson et al. | |
| 6,582,394 B1 | 6/2003 | Reiss et al. | |
| 6,582,459 B1 | 6/2003 | Lau et al. | |
| 6,596,020 B2 * | 7/2003 | Vardi et al. | 623/1.11 |
| 6,596,022 B2 | 7/2003 | Lau et al. | |
| 6,599,316 B2 | 7/2003 | Vardi et al. | |
| 6,645,241 B1 | 11/2003 | Strecker | |
| 6,682,556 B1 * | 1/2004 | Ischinger | 623/1.35 |
| 6,689,156 B1 | 2/2004 | Davidson et al. | |
| 6,692,483 B2 * | 2/2004 | Vardi et al. | 604/529 |
| 6,706,062 B2 | 3/2004 | Vardi et al. | |
| 6,733,487 B2 * | 5/2004 | Keith et al. | 604/526 |
| 6,749,628 B1 * | 6/2004 | Callol et al. | 623/1.15 |
| 6,905,477 B2 | 6/2005 | McDonnell et al. | |
| 2001/0012927 A1 | 8/2001 | Mauch | |

(56) References Cited

U.S. PATENT DOCUMENTS

| | | |
|---|---|---|
| 2001/0016767 A1 | 8/2001 | Wilson et al. |
| 2001/0016768 A1 | 8/2001 | Wilson et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037146 A1 | 11/2001 | Lau et al. |
| 2001/0037147 A1 | 11/2001 | Lau et al. |
| 2001/0039395 A1 | 11/2001 | Mareiro et al. |
| 2001/0039448 A1 | 11/2001 | Dibie |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Bockstegers et al. |
| 2002/0035392 A1 | 3/2002 | Wilson |
| 2002/0042650 A1 | 4/2002 | Vardi et al. |
| 2002/0052648 A1 | 5/2002 | McGuckin et al. |
| 2002/0058990 A1 | 5/2002 | Jang |
| 2002/0072790 A1 | 6/2002 | McGuckin et al. |
| 2002/0107564 A1 | 8/2002 | Cox et al. |
| 2002/0111675 A1 | 8/2002 | Wilson |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | Von Oepen |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1 | 12/2002 | Callol et al. |
| 2002/0193872 A1 | 12/2002 | Trout et al. |
| 2002/0193873 A1 | 12/2002 | Brucker et al. |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0050688 A1 | 3/2003 | Fischell et al. |
| 2003/0074047 A1 | 4/2003 | Richter |
| 2003/0093109 A1 | 5/2003 | Mauch |
| 2003/0114912 A1 | 6/2003 | Sequin et al. |
| 2003/0114915 A1 | 6/2003 | Mareiro et al. |
| 2003/0125791 A1 | 7/2003 | Sequin et al. |
| 2003/0125799 A1 | 7/2003 | Limon et al. |
| 2003/0125802 A1 | 7/2003 | Callol et al. |
| 2004/0015227 A1 | 1/2004 | Vardi et al. |
| 2004/0049259 A1 | 3/2004 | Strecker |
| 2004/0072849 A1 | 4/2004 | Schreiber et al. |
| 2004/0133268 A1 | 7/2004 | Davidson et al. |
| 2004/0138737 A1 | 7/2004 | Davidson et al. |
| 2004/0148006 A1 | 7/2004 | Davidson et al. |
| 2006/0100694 A1* | 5/2006 | Globerman .................. 623/1.35 |

FOREIGN PATENT DOCUMENTS

| | | |
|---|---|---|
| DE | 29701758 | 5/1997 |
| EP | 551179 | 7/1993 |
| EP | 684022 | 11/1995 |
| EP | 804907 | 5/1997 |
| EP | 876805 | 11/1998 |
| EP | 884028 | 12/1998 |
| EP | 891751 | 1/1999 |
| EP | 897698 | 2/1999 |
| EP | 897700 | 2/1999 |
| EP | 904745 | 3/1999 |
| EP | 1031328 | 8/2000 |
| EP | 1031330 | 8/2000 |
| EP | 1157674 | 11/2001 |
| EP | 646365 | 1/2004 |
| FR | 2678508 | 1/1993 |
| WO | WO 88/06026 | 8/1988 |
| WO | WO 90/13332 | 11/1990 |
| WO | WO 91/12779 | 9/1991 |
| WO | WO 92/19308 | 11/1992 |
| WO | WO 95/08985 | 4/1995 |
| WO | WO 95/21592 | 8/1995 |
| WO | WO 96/29955 | 10/1996 |
| WO | WO 96/41592 | 12/1996 |
| WO | WO 97/09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/03426 * | 1/1999 |
| WO | WO 99/15103 | 4/1999 |
| WO | WO 99/17680 | 4/1999 |
| WO | WO 99/34749 | 7/1999 |
| WO | WO 99/36002 | 7/1999 |
| WO | WO 99/39661 | 8/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/68012 | 9/2002 |
| WO | WO 02/78333 | 10/2002 |
| WO | WO 02/94336 | 11/2002 |
| WO | WO 03/055414 | 7/2003 |

OTHER PUBLICATIONS

Fischmann et al., *The New England Journal of Medicine*, vol. 331, No. 8, pp. 496-501 (1994).

Nakamura et al., *Catheterization & Cardiovascular Diagnosis* 34-353-361 (1995).

Caputo et al., *The American Journal of Cardiology*, vol. 7, pp. 1226-1230 (1996).

Colombo et al., *Catheterization and Cardiovascular Diagnosis*, vol. 30, pp. 327-330 (1993).

Carrie et al., *Catheterization and Cardiovascular Diagnosis*, vol. 37, pp. 311-313 (1996).

Katoh et al., *Catheterization and Cardiovascular Diagnosis*, vol. 40, pp. 400-402 (1997).

Lewis et al., *American Heart Journal*, vol. 127, pp. 1600-1607 (1994).

Dichek, D.A. et al.; *Circulation*, 80: 1347-1353 (1989).

Chevalier, B. et al.; *American Journal of Cardiology*, 82: 943-949 (1998).

Yamashita, T. et al.; *Journal of American College of Cardiology*, 35: 1145-1151 (2000).

Satler, S., et al.; *Catheterization and Cardiovascular Interventions*, 50: 411-412 (2000).

* cited by examiner

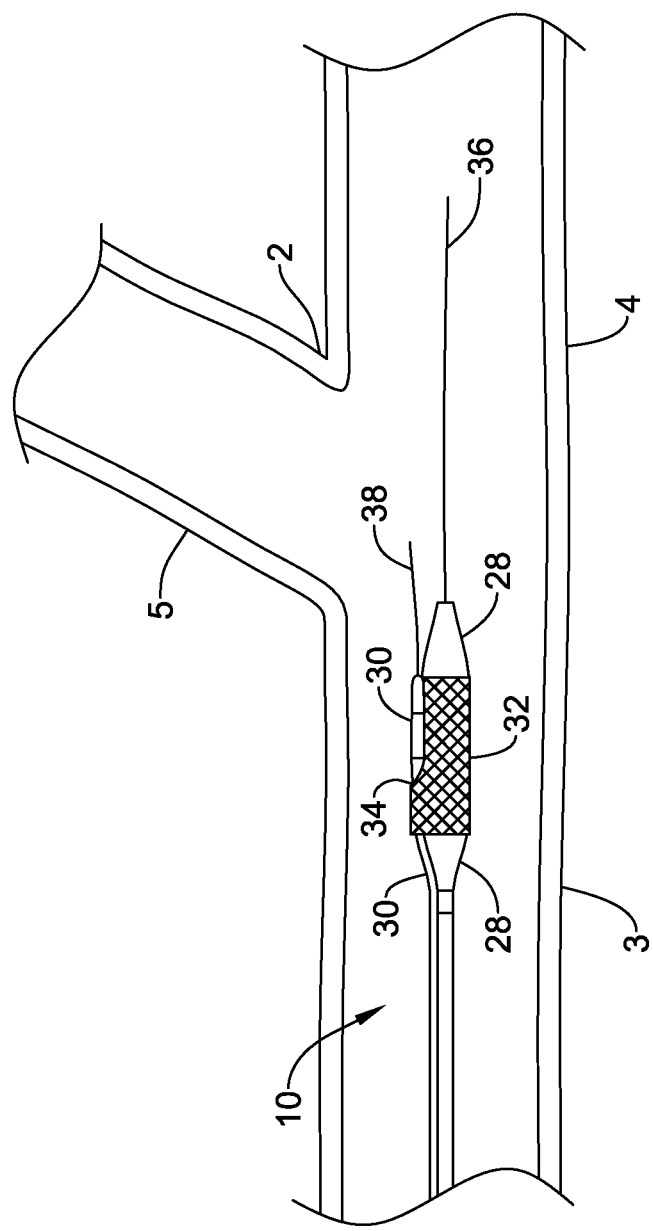

DUAL GUIDEWIRE EXCHANGE CATHETER SYSTEM

This application claims the benefit of U.S. Provisional Patent Application Ser. No. 60/413,552, filed Sep. 26, 2002, the disclosure of which is incorporated by reference herein in its entirety.

The disclosure of U.S. patent application Ser. No. 09/860,744, filed May 18, 2001, also is incorporated by reference herein in its entirety.

FIELD AND BACKGROUND OF THE INVENTION

The present invention relates generally to the field of medical catheters, and more specifically to a catheter used to deliver medical stents. In one aspect, the invention further relates to methods for deploying stents in vessels such that a side opening in the stent wall is aligned with an ostium of a branch vessel. In other aspects, the invention is related to the management of guidewires over which such catheters are introduced.

A stent is a type of endoprosthesis device, typically intraluminally placed or implanted within a vein, artery, or other tubular body organ for treating an occlusion, stenosis, aneurysm, collapse, dissection, or weakened, diseased, or abnormally dilated vessel or vessel wall, by expanding the vessel or by reinforcing the vessel wall. In particular, stents are quite commonly implanted into the coronary, cardiac, pulmonary, neurovascular, peripheral vascular, renal, gastrointenstinal and reproductive systems, and have been successfully implanted in the urinary tract, the bile duct, the esophagus, the tracheo-bronchial tree and the brain, in order to reinforce these body organs. Two important currant widespread applications for stents are for improving angioplasty results by preventing elastic recoil and remodeling of the vessel wall and for treating dissections in blood vessel walls caused by balloon angioplasty of coronary arteries as well as peripheral arteries. Conventional stents have been used for treating more complex vascular problems, such as lesions at or near bifurcation points in the vascular system, where a secondary artery branches out of a larger, main artery, with limited success rates, as described by Chevalier, B., et al., in the American Journal of Cardiology, 82: 943-949, 1998; Yamashita, T., et al., in the Journal of American Coll ge of Cardiology, 35: 1145-1151, 2000; and Satler, S., et al., in Catheterization and Cardiovascular Interventions, 50: 411-412, 2000.

Conventional stent designs typically feature a straight tubular, single type cellular structure, configuration, or pattern which is repetitive through translation along the longitudinal axis, and sometimes also along the radial axis of the stent. The repeating structure, configuration, or pattern has strut and connecting members that can impede blood flow at bifurcations. Furthermore, the configuration of struts and connecting members may obstruct the use of post-operative devices to treat a branch vessel in the region of a vessel bifurcation. For example, a physician may be unable to insert a branch stent through the ostium of a branch vessel of a vessel bifurcation in cases where treatment of the main vessel is suboptimal as a result of displacing diseased tissue (plaque shifting or 'snow plowing'), occlusion, vessel spasm, dissection with or without intimal flaps, thrombosis, embolism, and/or other vascular diseases. Accordingly, the use of regular stents to treat diseased vessels at or near a vessel bifurcation may create a risk of compromising the degree of patency of the main vessel, branch vessels, and/or the bifurcation point.

Non-conventional stents, such as a stent with a side opening for branch vessel access, or double stenting systems can be used to overcome some of the above limitations. Delivery of such non-conventional stents often requires the use of non-conventional catheters. For example, catheters with two lumens for guidewires—a main guidewire lumen and a branch guidewire lumen—are used to deliver stents with side branch access. Examples of such catheters are described, for example, in co-pending U.S. application Ser. No. 09/663,111, filed Sep. 15, 2000 and co-pending U.S. application Ser. No. 09/455,299, filed Dec. 6, 1999, both of which are incorporated herein by reference in their entireties.

However, the use of such non-conventional stents and catheters produces additional challenges, resulting from the use of more than one guidewire. After a guidewire is appropriately positioned within the patient body, a trailing end portion of the guidewire typically extends out of the patient body from the point of entry. It has been found that the trailing end portion of the guidewire outside the patient body can be rather difficult to manage and can interfer with the efficiency of the medical procedure performance. This is especially true when more than one guidewire is being used during a medical procedure. In such a case, the medical practitioner performing the procedure may confuse the trailing end portions of the guidewires protruding from the patient body with one another. Furthermore, long wires are difficult to manage and often require more than one individual for proper manipulation. This problem is exacerbated when more than one long wire is used.

When using multiple wires to introduce a catheter system, one condition that may occur is known as "wire crossing." In such cases, the guidewires over which the catheter system is advanced intertwine within the guide catheter and vasculature. This condition may prevent the successful delivery of the catheter system by impeding its travel and subsequently, the alignment of the stent's side opening with the ostium of the branch vessel.

There is thus a widely recognized need for, and it would be highly advantageous to have, a dual guidewire catheter system that avoids the above limitations.

SUMMARY OF THE INVENTION

According to one aspect of the present invention, there is provided a catheter system for positioning a stent at a vessel bifurcation. The catheter system includes a catheter having a channel with a main guidewire lumen extending proximally from a distal end of the catheter to a main exit port located at a first distance from the distal end, wherein the main guidewire lumen is configured to receive a main vessel guidewire therethrough, a branch guidewire enclosure positioned alongside the channel and extending proximally from the side opening of the stent to a branch exit port located at a second distance from the distal end of the catheter system, wherein the branch guidewire lumen is configured to receive a branch vessel guidewire therethrough, and a stent having a lumen and a side opening in a wall thereof, the stent positioned on a distal portion of the channel, and wherein a distal portion of the branch guidewire enclosure is positioned through the lumen and exiting at the side opening, wherein at least one of the distances is less than a distance from the distal end of the catheter system to a proximal end of the catheter system and greater than a distance from the distal end of the catheter system to the proximal end of the stent.

According to another aspect of the present invention, there is provided a catheter having a proximal tube portion, a distal portion having a first lumen and a second lumen, wherein the first lumen is configured to receive a first guidewire and the second lumen is configured to receive a second guidewire, and a bond portion connecting the proximal portion with the distal portion, wherein the bond portion includes a three-way bond.

According to another aspect of the present invention, there is provided a method of inserting a catheter system into a bifurcated body lumen having a main vessel and a branch vessel. The method includes providing a catheter having a channel with a main guidewire lumen configured to receive a main vessel guidewire therethrough and a branch guidewire lumen positioned alongside the channel configured to receive a branch vessel guidewire therethrough, providing a first guidewire having a proximal end and a distal end and a length of less than 50 centimeters, and a second guidewire having a proximal end and a distal end and a length of less than 50 centimeters, inserting the first guidewire into a first vessel, inserting the second guidewire into the first vessel, inserting the proximal end of the first guidewire into the main guidewire lumen of the catheter, inserting a proximal end of the second guidewire into the branch guidewire lumen of the catheter, advancing the catheter over the first guidewire and the second guidewire into the body lumen until a vicinity of the bifurcation, retracting the second guidewire until the distal end of the second guidewire is in the vicinity of the bifurcation, advancing the second guidewire into the branch vessel, and advancing the catheter over the first and second guidewires.

According to further features in preferred embodiments of the invention described below, the catheter system includes a balloon disposed on the channel and through the lumen of said stent, the balloon being for expansion of the stent, and the channel includes an inflation portion for inflating the balloon.

According to still further features in preferred embodiments of the invention described below, the catheter system includes a bond portion connecting the main exit port and branch exit port to a proximal tube, the proximal tube extending proximally from the bond portion to the proximal end of the catheter system.

According to still further features in preferred embodiments of the invention described below, the first distance is between 10 and 50 centimeters, the second distance is between 10 and 50 centimeters and the first distance is approximately equal to the second distance. Alternatively, the first distance is between 10 and 50 centimeters and the second distance is between 50 and 150 centimeters, and the branch guidewire enclosure extends proximally to the proximal end of said catheter. In one aspect, the branch guidewire enclosure is a side sheath.

According to still further features in preferred embodiments of the invention described below, the catheter system includes a main vessel guidewire and a branch vessel guidewire which are less than 50 centimeters in length.

According to still further features in preferred embodiments of the invention described below, the first and second lumens are attached along their entire lengths, or only at the bond portion. The bond portion is located at a predetermined distance from a proximal portion of the stent, wherein the distance is between 5 and 15 centimeters.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and arc presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 5A-5G are illustrations of the steps of a method of inserting a catheter such as the one shown in FIG. 1 into a bifurcated body lumen and further deploying a stent therein;

DESCRIPTION OF THE PREFERRED EMBODIMENTS

Figure 1:
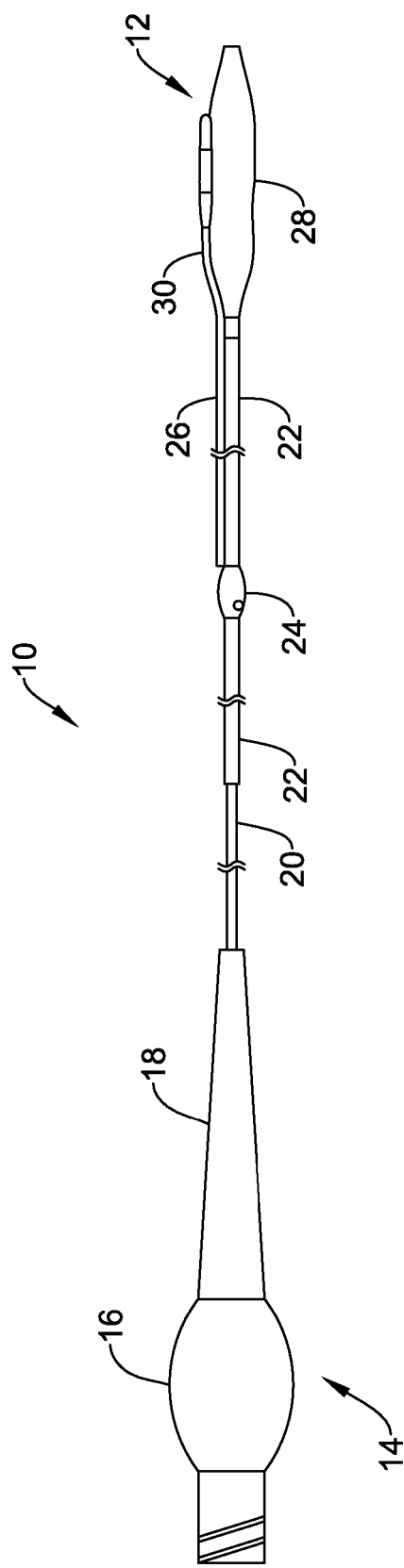
FIG. 1 is an elevational view of a dual guidewire exchange catheter system in accordance with a preferred embodiment of the present invention.

The present invention is of a dual guidewire exchange catheter system for delivery of a stent with a side opening, which cain be delivered to a vessel bifurcation. Specifically, the present invention can be used to deliver a stent to a vessel bifurcation while controlling guidewire management.

The principles and operation of a dual guidewire exchange catheter according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Reference is now made to FIG. 1, which is an elevational view of a dual guidewire exchange catheter system 10 in accordance with a preferred embodiment of the present invention. Catheter system 10 has a distal end 12 and a proximal end 14. At proximal end 14, catheter system 10 includes a luer hub 16 with a strain relief portion 18. A hypotube 20 xtends along most of the I ngth of catheter system 10, followed by an inflation tube 22 with a bond portion 24, and a distal shaft 26 positioned alongside inflation tube 22 in a region distal to bond portion 24. Inflation tube 22 leads into a balloon 28, while distal shaft 26 leads into a side sheath 30 positioned alongside balloon 28. According to one embodiment of the present invention, the length of catheter system 10 from proximal end 14 to distal end 12 is between 100 cm and 200 cm. In a preferred embodiment, the length of catheter system 10 from proximal end 14 to distal end 12 is approximately 140-150 cm.

In a preferred embodiment, luer hub 16 is comprised of a polymer material, such as polycarbonate, acrylic, or any other suitable material, and strain relief portion 18 is comprised of silicone. Strain relief portion 18 provides a transition between the relatively stiff luer hub 16 and the less stiff hypotube. As such, any suitable polymer with an intermediate stiffness may be used. In a preferred embodiment, coated hypotube 20 is comprised of a biocompatible metal, such as stainless steel, titanium, cobalt-chromium, or any other suitable material. In one embodiment, hypotube 20 is coated with a polymer such as polyethylene, Pebax, nylon or others. In one embodiment, hypotube 20 has a hollow interior, with an inner diameter of 0.01-0.02 inches and an outer diameter of 0.02-0.04 inches. In a preferred embodiment, hypotube 20 has an inner diameter of 0.012-0.019 inches and an outer diameter of 0.025-0.031 inches. Inflation tube 22 is sealed to and surrounds hypotube 20 at an intermediate point along the length of hypotube 20. In a preferred embodiment, inflation tube 22 is comprised of a mixture of Pebax (approximately 96%) and granite (approximately 4%), although in alternative embodiments it can be comprised of any suitable polymer or combination of materials. Bond portion 24 is attached to inflation tube 22 at a point distal to the proximal end of inflation tube 22. Details of bond portion 24 will be described hereinbelow with respect to FIG. 2.

Distal to bond portion 24, distal shaft 26 is positioned alongside inflation tube 22. Distal shaft 26 is comprised of a polymer or composite material. In a preferred embodiment, distal shaft 26 is comprised of Nylon 12 and Vestamid L2124. Many different attachment configurations for distal shaft 26 and inflation tube, leading into side sheath 30 and balloon 28, respectively, are envisioned. In one embodiment, distal shaft 26 is attached to inflation tube 22 but side sheath 30 is detached from balloon 28. In another embodiment, distal shaft 26 is attached to inflation tube 22 along its length and side sheath 30 is at least partially attached to balloon 28. In yet another embodiment, distal shaft 26 is only attached to inflation tube 22 at a specific point or points along its length, and is detached from inflation tube 22 at other portions. For example, distal shaft 26 can be attached to inflation tube 22 in the region of bond portion 24 and at a point just proximal to balloon 28. Alternatively, distal shaft 26 can be attached to inflation tube 22 only in the region of bond portion 24.

Figure 2:
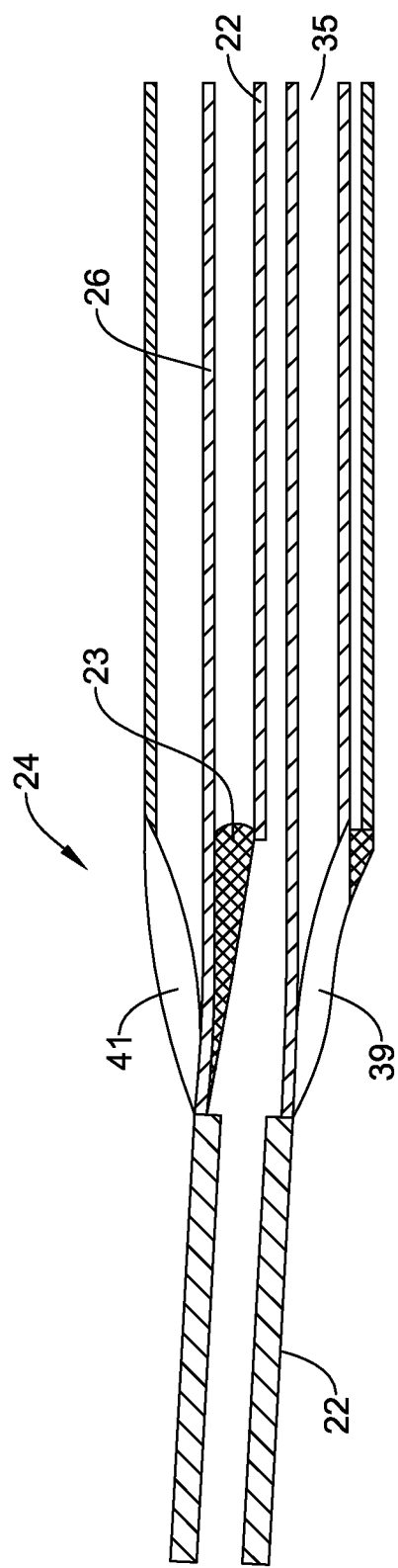
FIG. 2 is an illustration of the bond portion of the catheter of FIG. 1.

Reference is now made to FIG. 2, which is an illustration of bond portion 24 in greater detail. Bond portion 24 is a three-way bond, connecting one portion of tubing (inflation tube 22) on the proximal end of bond portion 24 and two portions of tubing (inflation tube 22 and a distal shaft 26) on the distal end of bond portion 24. As shown in FIG. 2, a bonding area 23 connects distal shaft 26 to inflation tube 22. In a preferred embodiment, the materials in the bond portion are nylon/Pebax and are thermally fused together to form the bond.

Figure 3:
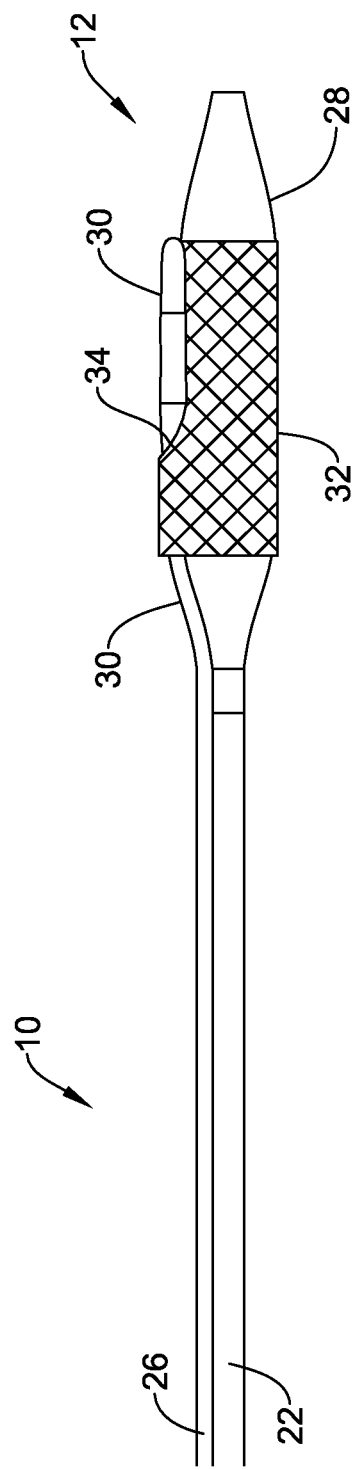
FIG. 3 is an elevational view of a region of the catheter of FIG. 1 distal to the bond portion illustrated in FIG. 2.

Reference is now made to FIG. 3, which is an elevational view of a region of catheter 10 which is distal to bond portion 24, having a stent 32 positioned on balloon 28. Stent 32 is a metallic mesh with a configuration of struts and connectors, which is positioned on balloon 28 in an unexpanded state, and which can be expanded once in place within a vessel so as to provide support to the walls of the vessel and allow for unobstructed flow of blood. Stent 32 En be any suitable stent, such as the ones described in, for example, co-pending U.S. application Ser. No. 09/600,348, filed Jul. 14, 2000, co-pending U.S. application Ser. No. 09/963,114, filed Sep. 24, 2001 and PCT International Application Serial Number IL02/00840, filed Oct. 20, 2002, all of which are incorporated herein by reference in their entireties. Stent 32 further includes a side opening 34, through which side sheath 30 is positioned so as to allow side sheath 30 to be positionable in a vessel bifurcation In an alternative embodiment, side sheath 30 is positioned at side opening 34 of stent 32 and does not protrude therethrough, but allows a guidewire placed therein to be positioned through side opening 34 and into a branch vessel. The relative lengths of tubing distal to bond portion 24 can be seen in FIG. 3. It should be readily apparent, however, that the lengths may vary. In one embodiment, the length of distal shaft 26 and inflation tube 22 from bond portion 24 until balloon 28 is 1-100 cm. In an exemplary preferred embodiment, the length of distal shaft 26 and inflation tube 22 from bond portion 24 until balloon 28 is approximately 30 cm. By distancing the balloon and stent from bond portion 24 (by around 10 cm or more), more flexibility in rotation of the system is provided, facilitating rotational alignment of side opening 34 of stent 32 with the ostium of the branch vessel. Furthermore, stiffness in the area of the stent is reduced by not having extra bond material present in the gen ral region of the stent.

Figure 4:
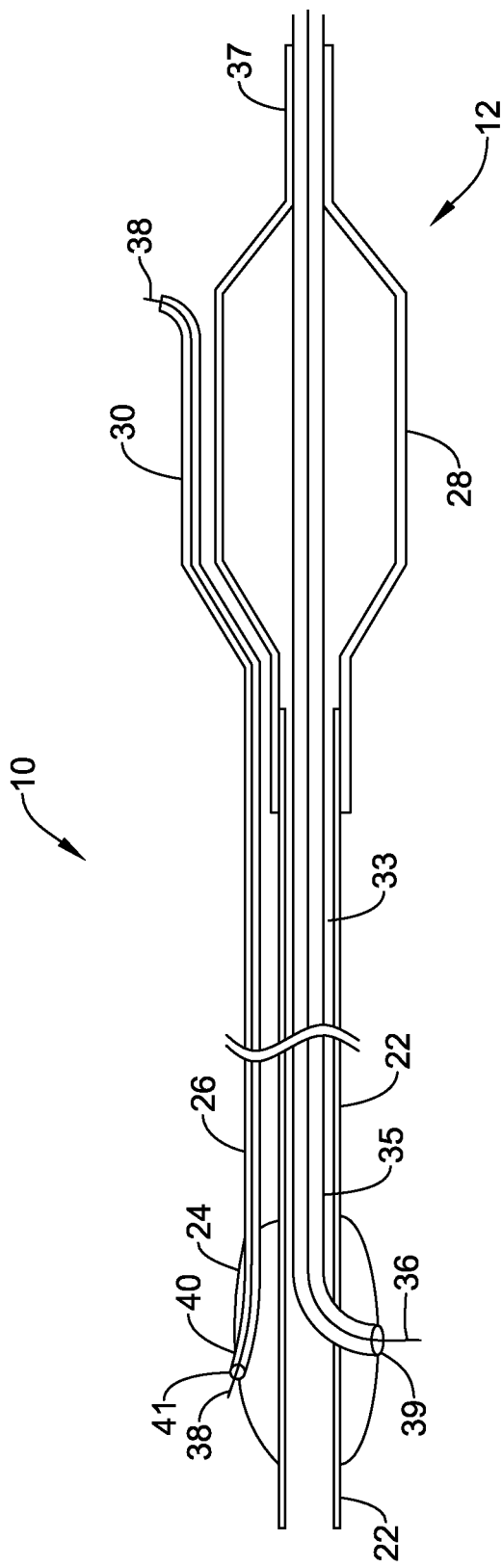
FIG. 4 is a cross section illustration of the catheter in the region of FIG. 3.
Figure 7:
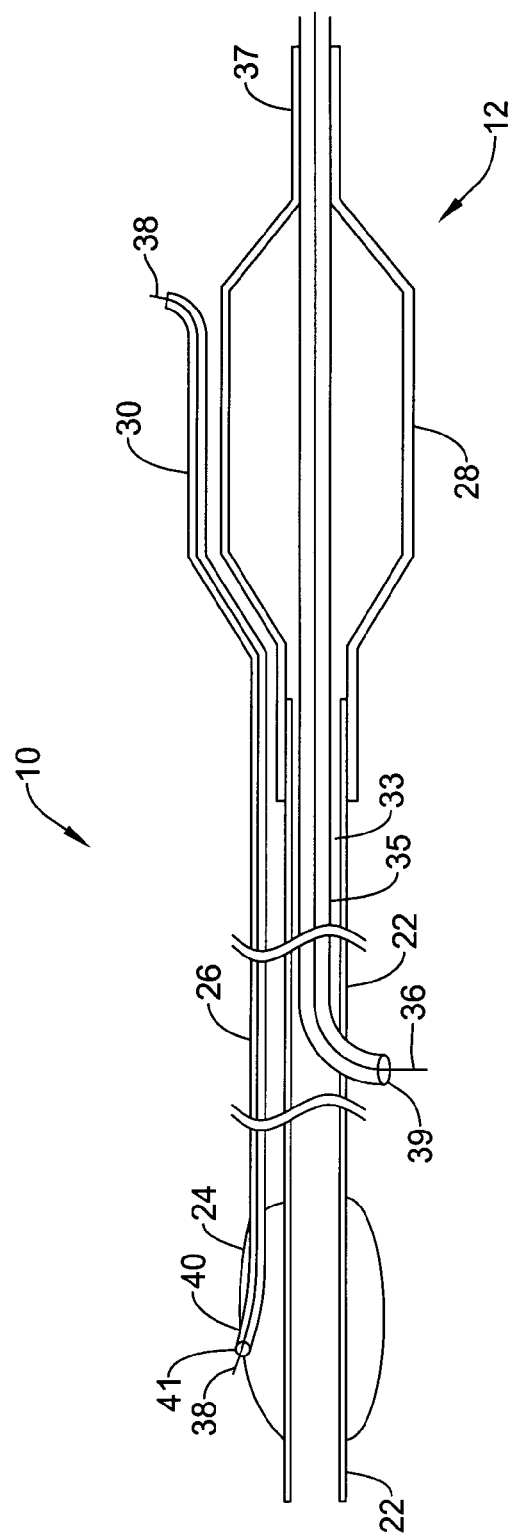
FIG. 7 is a cross section illustration of a catheter in accordance with another embodiment of the invention.

Reference is now made to FIG. 4, which is a cross-section illustration of the region of catheter 10 shown in FIG. 3 Inflation tube 22 has a main guidewire lumen 35, wherein main guidewire lumen 35 has a smaller diameter than that of inflation tube 22. This configuration allows communication via a fluid communication zone 33 between inflation tube 22 and the inside of balloon 28, through which inflation fluid may be provided to balloon 28, thus allowing balloon 28 to expand. Main guidewire lumen 35 extends from a main guidewire exit port 39 to distal end 12 of catheter system 10, exiting through a tip 37 of catheter 10. A main vessel guidewire 36 can be positioned within main guidewire lumen 35, wherein a distal portion of main vessel guidewire 36 is positionable within the main vessel. Since main guidewire exit port 39 is a relatively short distance from tip 37, a relatively short length of main guidewire 36 is needed, in a range of, for example, 3-35 cm, particularly as compared to an over-the-wire system, wherein the main guidewire lumen would extend along the entire length from tip 37 to the proximal end of a catheter. Similarly, distal shaft 26 includes a branch vessel guidewire lumen 40, which extends from a branch vessel guidewire exit port 41 to the distal end of side sheath 30. A branch vessel guidewire 38 can be positioned within branch vessel guidewire lumen 40, wherein a distal portion of branch vessel guidewire 38 is positionable within a branch vessel. Since branch vessel guidewire exit port 41 is a relatively short distance from the distal end of side sheath 30, a relatively short length of branch vessel guidewire 38 is needed, in a range of, for example, 3-35 cm, particularly as compared to a system wherein the branch vessel guidewire lumen would extend along the entire length from side sheath 30 to the proximal end of a catheter. Thus, catheter 10 has dual guidewire exchange capability, in that either main vessel guidewire 36 or branch vessel guidewire 38 or both may be relatively short in length, allowing for management of shorter wires outside of the body. In an alternative embodiment, shown in FIG. 7, the locations of exit ports 39 and 41 are located apart from one another along the length of the system. This configuration would enable reduction of the profile of the overall system.

Figure 5A:
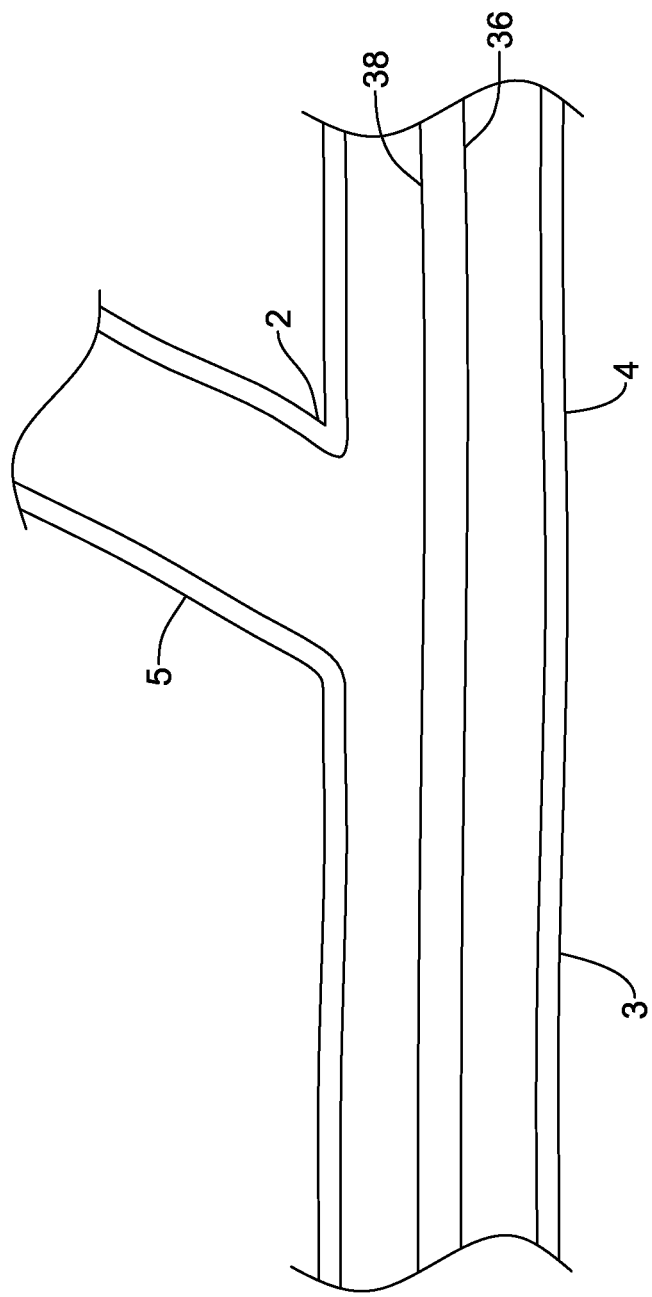
Figure 5B:
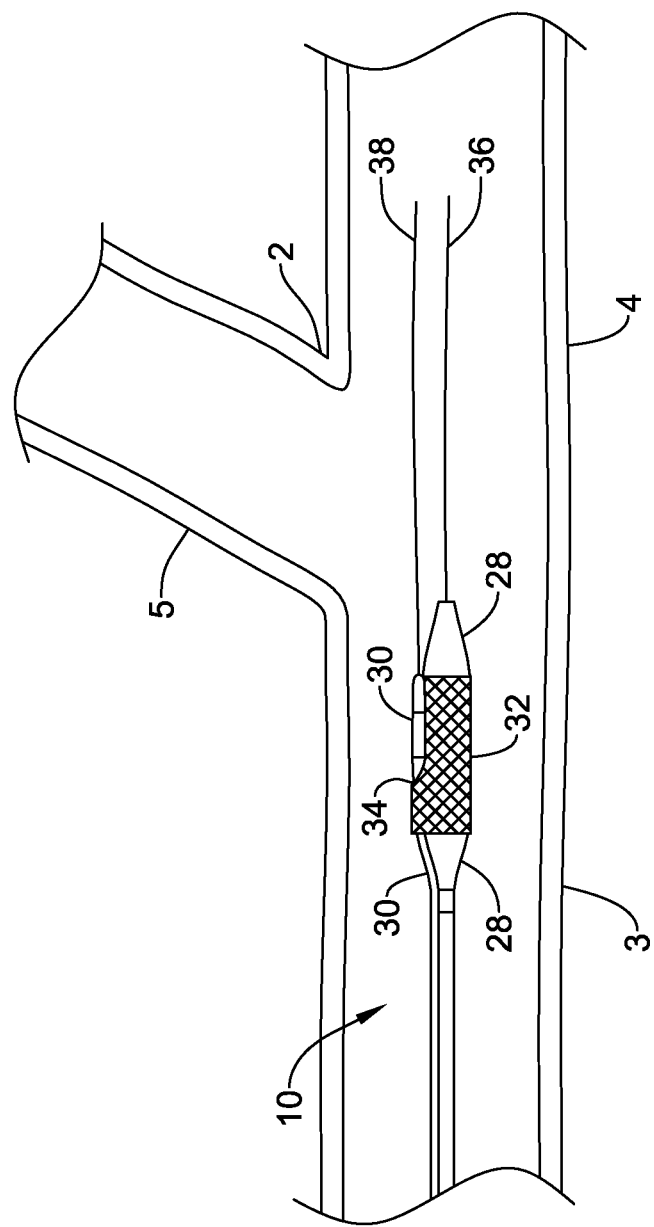
Figure 5D:
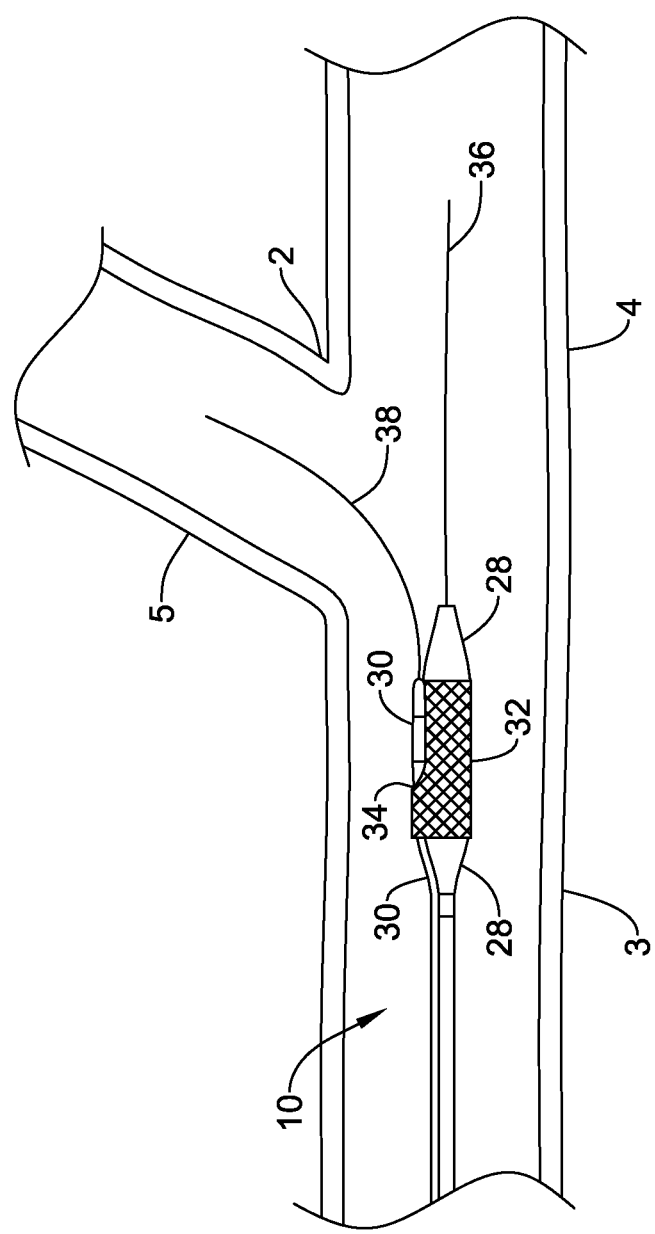
Figure 5E:
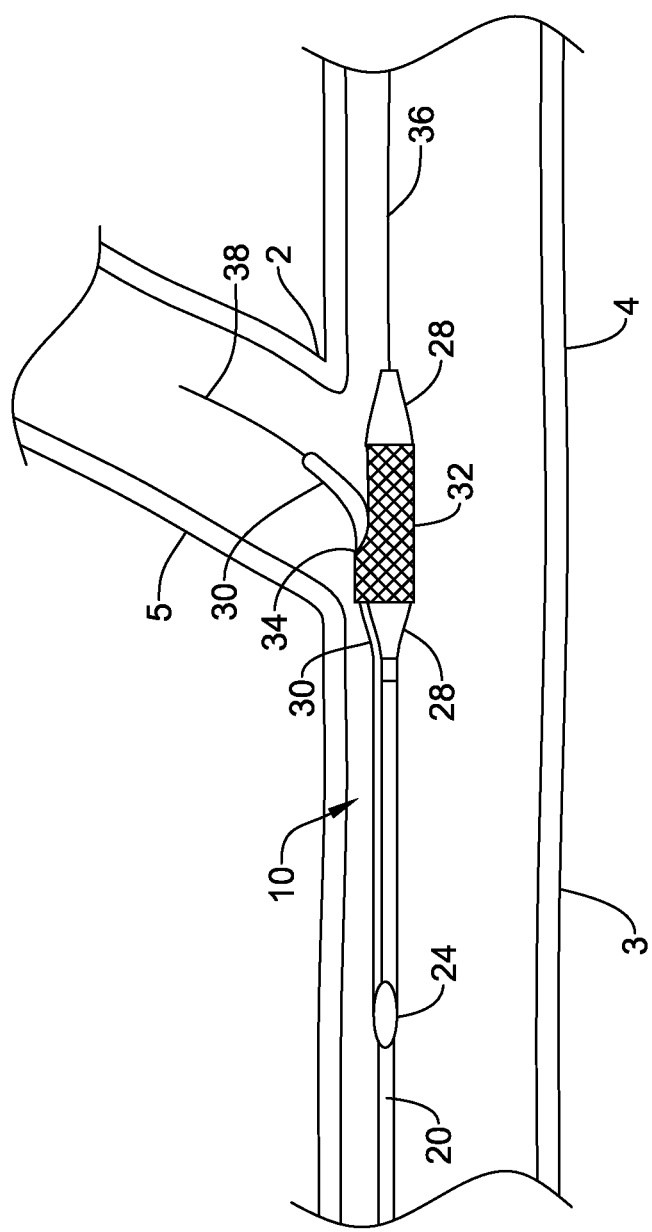
Figure 5F:
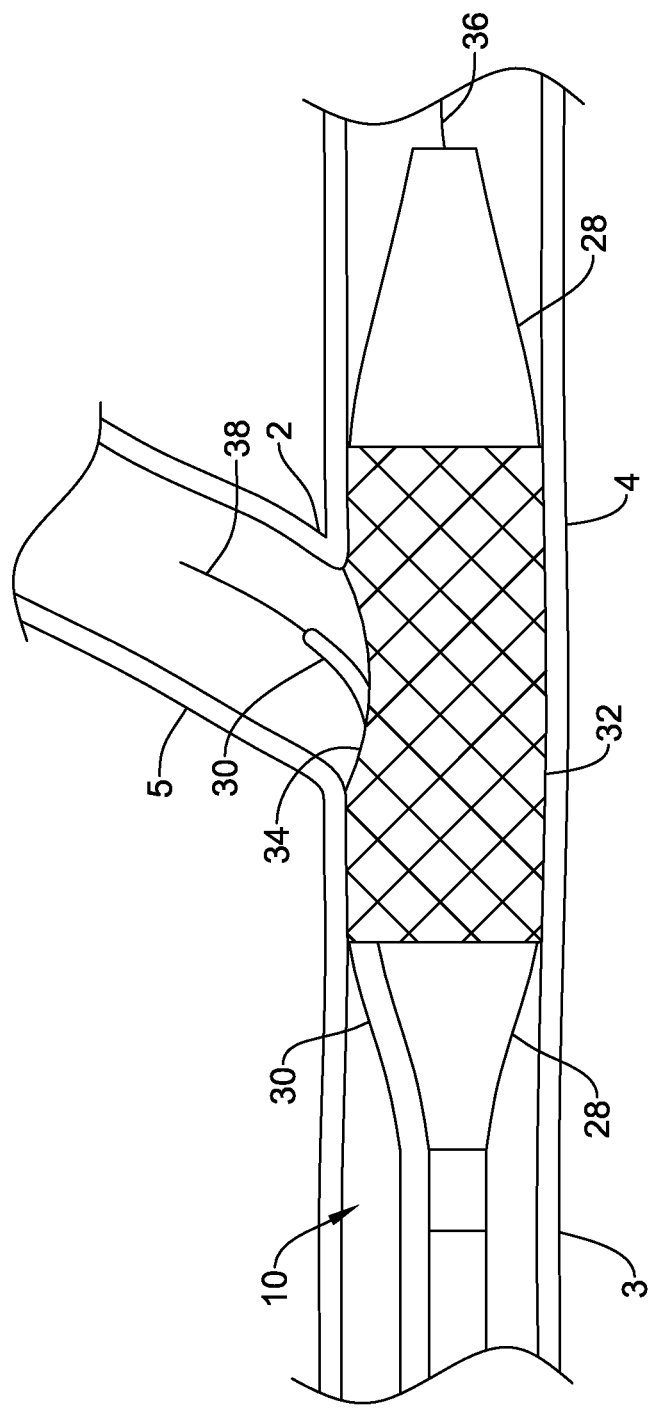
Figure 5G:
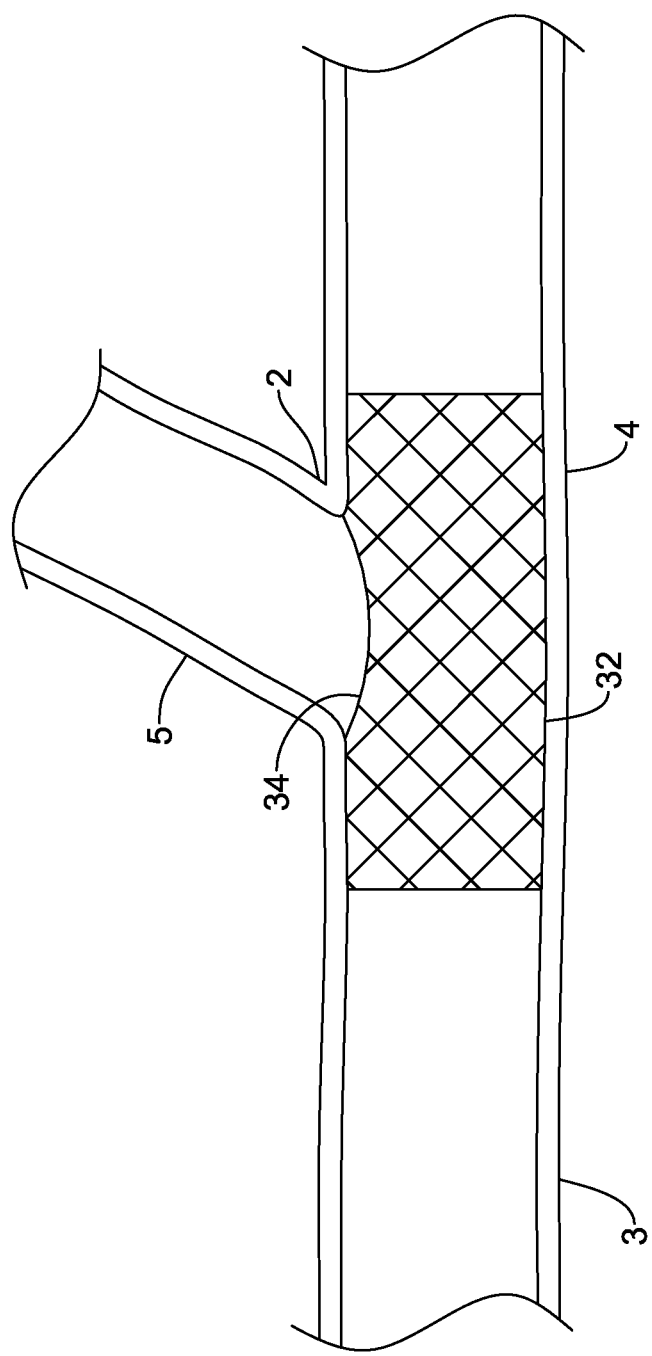

Suitable methods for advancing a dual guidewire exchange catheter system such as the one described hereinabove are described and illustrated in FIGS, 5A-5G and 6A-6B. Reference is made first to FIGS. 5A-5G, which are illustrations of the steps of inserting catheter system 10 into a bifurcated body lumen and expanding stent 32 therein, in accordance with a preferred embodiment of the present invention. FIGS. 5B-5F illustrate catheter system 10, to be deployed in a bifurcation 2, wherein a main vessel 3 is split into a main vessel continuation 4 and a branch vessel 5. As shown in FIG. 5A, both main vessel guidewire 36 and branch vessel guidewire 38 are initially placed in the main vessel 3, preferably extending into main vessel continuation 4. Optionally, a safety guidewire (not shown) can be inserted into the branch vessel for reference and for support of the branch vessel. As shown in FIG. 5B, catheter system 10 is then advanced over both vessel guidewires, with main vessel guidewire 36 being positioned through main guidewire lumen 35 of catheter system 10 and with branch vessel guidewire 38 being positioned through side sheath 30 and branch vessel guidewire lumen 40 of catheter system 10. It should be readily apparent that by using a system such as the one described above, shorter lengths of either or both vessel guidewires can be used, since only a relatively short amount of wire is needed outside of the body for threading into the system. This provides ease of maneuverability of wires outside of the body. Additionally, since the wires can more easily be manipulated, this can lead to greater control of the wires within the body, possibly reducing wire entanglement As shown in FIG. 5C, branch vessel guidewire 38 is then retracted until its tip is opposite or proximal to the ostium of branch vessel 5. Subsequently, as shown in FIG. 5D, branch vessel guidewire 38 is advanced into branch vessel 5. If a safety wire is present, it is removed at this point. Next, as shown in FIG. 5E, catheter system 10 is advanced over both wires until stent 32 is in its optimal position with respect to the ostium of the bifurcation. Balloon 28 is then expanded by introducing fluid into balloon 28 via inflation tube 22, wherein the expansion of balloon 28 causes stent 32 to be deployed, as shown in FIG. 5F. Finally, as shown in FIG. 5G, catheter system 10 and guidewires 36 and 38 are removed, leaving only the expanded stent 32 in place.

In an alternative embodiment, both guidewires 36, 38 are initially placed in the branch vessel 5, and catheter system 10 is advanced over the two wires In the alternative embodiment just described, main vessel guid wire 36 is retracted and subsequently advanced through main vessel 3 and into main vessel continuation 4. By initially positioning both guidewires 36 and 38 in the same vessel, crossover and entanglement of the wires may be fitter minimized.

Figure 6A:
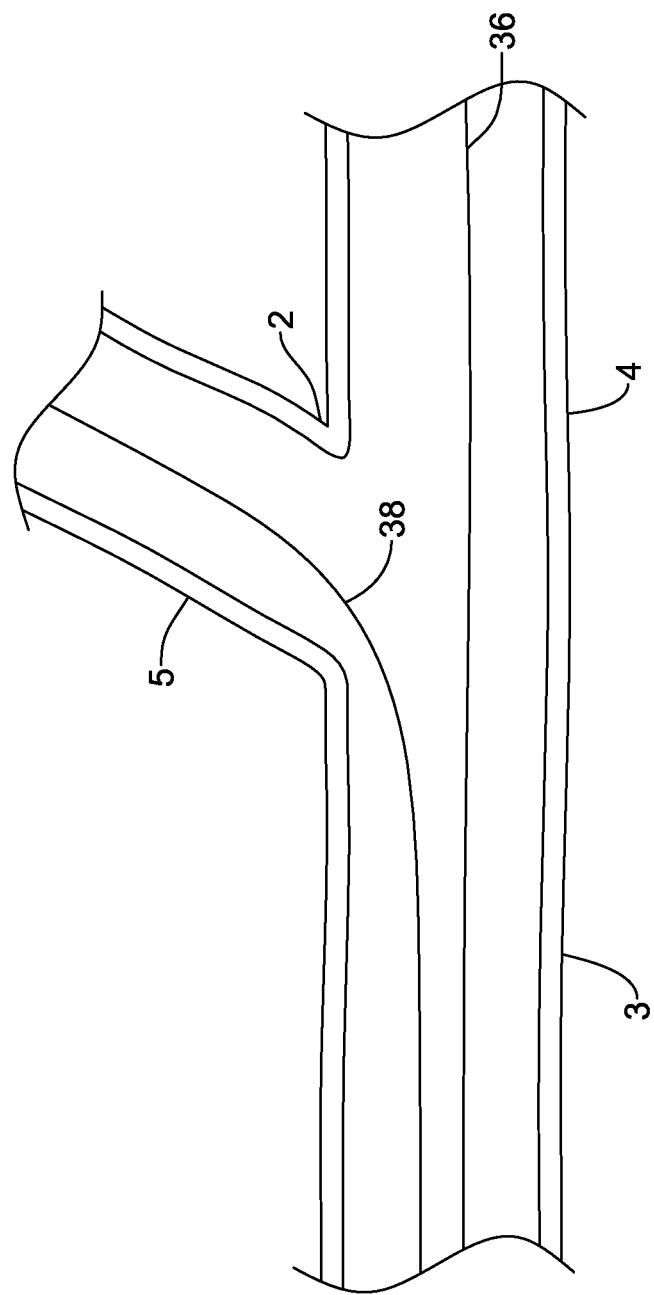
FIGS. 6A-6B are illustrations of the steps of an alternative method of inserting a catheter such as the one shown in FIG. 1 into a bifurcated body lumen.
Figure 6B:
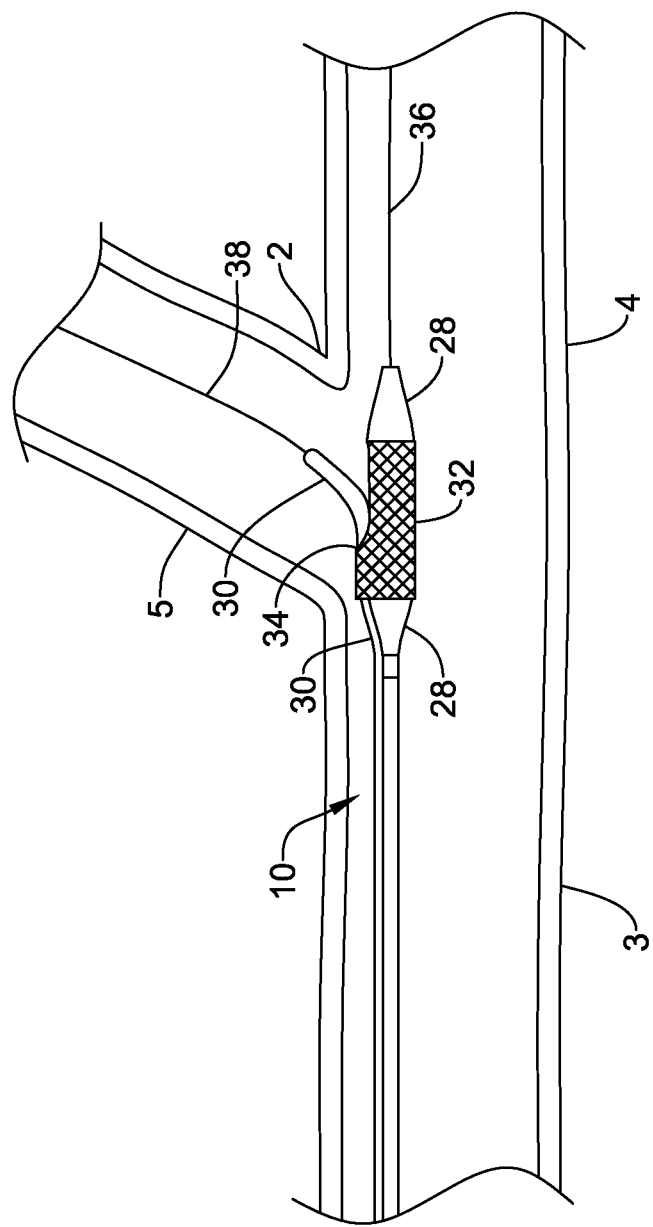

Reference is now made to FIGS. 6A and 6B, which are illustrations of the steps of an alternative method of advancing a dual lumen dual side exchange system such as the one described hereinabove. As shown in FIG. 6A, initially main vessel guidewire 36 is positioned within main vessel 3 and into main vessel continuation 4, and branch vessel guidewire 38 is positioned within main vessel 3 and into branch vessel continuation 5. Following initial placement of wires 36 and 38, catheter system 10 is advanced by backloading main vessel guidewire 36 into main guidewire lumen 35 in catheter system 10, and branch vessel guidewire 38 into side sheath 30 and branch vessel guidewire lumen 40 in catheter system 10. The main guidewire 36 and the branch guidewire 38, after being so placed, are then used for tracking the catheter system 10 to its proper position before deploying the stent 32, as depicted in FIG. 6B.

In alternative embodiments, a single side dual guidewire lumen catheter system 100 is envisioned, wherein either a branch vessel guidewire lumen or a main vessel guidewire lumen has an exit port relatively close to a distal end of the catheter system, and wherein the other lumen extends proximally along the length of the catheter system. Such systems are described in co-pending U.S. patent application Ser. No. 09/860,744, filed May 18, 2001, incorporated herein by reference in its entirety.

Several methods arc suitable for advancing a single side dual guidewire lumen catheter system to a bifurcation. For a system with a long main vessel guidewire lumen and a short branch vessel guidewire lumen, a main vessel guidewire is preloaded into the main vessel guidewire lumen, and a branch vessel guidewire is inserted into the main vessel or the branch vessel. The entire system is then advanced over the branch vessel guidewire, until the catheter is just proximal to the bifurcation. If the branch vessel guidewire is in the branch vessel, the main vessel guidewire is advanced into the main vessel and the entire system is advanced over both wires until the stent is properly positioned. If the branch vessel guidewire is in the main vessel, the branch vessel guidewire is retracted and then advanced into the branch vessel, after which the main vessel guidewire is advanced into the main vessel and the system is advanced over both wires.

For a system with a long branch vessel guidewire lumen and a short branch vessel guidewire lumen, a branch vessel guidewire is preloaded into the branch vessel guidewire lumen, and a main vessel guidewire is inserted into the main vessel. The entire system is then advanced over the main vessel guidewire, until the catheter is just proximal to the bifurcation. The branch vessel guidewire is then advanced into the branch vessel, and the system is advanced over both wires.

It is appreciated that certain features of the invention, which are, for clarity, described in the context of separate embodiment, may also be provided in combination in a single embodiment. Conversely, various features of the invention, which arc, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. For example, self-expanding stents may be used, wherein a balloon is not used. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A catheter system for positioning a stent at a vessel bifurcation, the catheter system comprising:
   a catheter including a proximal end and a distal end, the catheter comprising:
      a first tubular member including a proximal end and a distal end, the first tubular member defining an inflation lumen of the catheter and extending distally from the proximal end of the catheter;

a second tubular member defining a main guidewire lumen, wherein the distal end of the second tubular member is a distal end of the catheter and the proximal end of the second tubular member defines a main guidewire exit port, wherein the main guidewire lumen is configured to receive a main vessel guidewire therethrough, wherein the second tubular member is at least partially disposed within the inflation lumen of the first tubular member;

a balloon including a proximal waist coupled directly to the first tubular member adjacent to the distal end of the first tubular member and a distal waist coupled directly to the second tubular member adjacent to the distal end of the second tubular member;

a branch guidewire enclosure positioned alongside the first tubular member, wherein the branch guidewire enclosure defines a lumen configured to receive a branch vessel guidewire therethrough, the branch guidewire enclosure including a proximal end region having a proximal end, a distal end region, and an intermediate region disposed between the proximal end region and the distal end region, the proximal end of the branch guidewire enclosure defining a branch guidewire exit port; and a stent having a lumen and a side opening in a wall thereof, the stent positioned about at least a portion of the balloon, and wherein a distal portion of the branch guidewire enclosure is positioned through the lumen of the stent and exits at the side opening;

wherein the branch guidewire enclosure is bonded only to the first tubular member and only bonded to the first tubular member at a bond at the proximal end region of the branch guidewire enclosure, wherein the intermediate region of the branch guidewire enclosure is 10 cm to 100 cm in length between the bond and the proximal end of the balloon, wherein the main guidewire exit port and the branch guidewire exit port are located proximal of the stent and distal of the proximal end of the catheter.

2. The catheter system of claim 1, further comprising a bonding material coupling the first tubular member, second tubular member, and branch guidewire enclosure.

3. The catheter system of claim 1, wherein the main guidewire exit port is positioned between 10 and 50 centimeters from the distal end of the catheter.

4. The catheter system of claim 1, wherein the main guidewire exit port and the branch guidewire exit port are located at substantially the same longitudinal position along the catheter.

5. The catheter system of claim 1, wherein the distance between the proximal end of the branch guidewire enclosure and the proximal waist of the balloon is approximately 30 cm to 100 cm.

6. A catheter comprising:
a first catheter tube including a proximal end and a distal end;
a first distal tube having a proximal end region defining a proximal open end, the first distal tube being configured to receive a first guidewire;
a second distal tube having a proximal end region defining a proximal open end, the second distal tube being configured to receive a second guidewire;
a balloon including a proximal waist and a distal waist, the proximal waist being coupled directly to the first catheter tube adjacent the distal end of the first catheter tube, and the distal waist being coupled directly to the first distal tube adjacent to a distal end of the first distal tube;
a stent positioned about at least a portion of the balloon, wherein the second distal tube is configured to exit through a side opening in the stent; and
a bond material configured to form a bond between the proximal end region of the second distal tube and an intermediate region of the first catheter tube, wherein the proximal open end of the second distal tube remains open to define a second guidewire exit port, wherein the second distal tube is bonded only to the first catheter tube and is bonded to the first catheter tube only at the bond, and wherein the bond is spaced from the proximal end of the balloon by around 10 cm to 100 cm.

7. The catheter of claim 6, wherein the first and second guidewires are configured to exit the catheter at the proximal open ends of the first and second distal tubes.

8. The catheter of claim 6, wherein the first guidewire and the second guidewire are each less than 50 centimeters in length, and the bond is spaced from the proximal waist of the balloon by a distance suitable for use with first and second guidewires of less than 50 cm.

9. The catheter of claim 6, wherein the bond is spaced from the proximal waist of the balloon by approximately 30 cm to 100 cm.

10. The catheter of claim 6 wherein the second distal tube is detached from the first distal tube outside of the bond material.

11. The catheter of claim 6, wherein the second distal tube does not include a balloon.

12. The catheter of claim 6, wherein the proximal end of the first distal tube is disposed at or near the intermediate region of the first catheter tube and remains open to define a first guidewire exit port.

13. The catheter of claim 12, wherein the first distal tube is at least partially attached to the first catheter tube.

14. The catheter of claim 13, wherein the first distal tube is at least partially disposed within the first catheter tube.

15. The catheter of claim 12, wherein the first guidewire exit port and the second guidewire exit port are disposed at substantially the same longitudinal position along the catheter.

16. A catheter comprising:
a first catheter tube including a proximal end and a distal end;
a first distal tube having a proximal end region defining a proximal open end, the first distal tube being configured to receive a first guidewire;
a second distal tube having a proximal end region defining a proximal open end, the second distal tube being configured to receive a second guidewire;
a balloon including a proximal waist and a distal waist, the proximal waist being coupled directly to the first catheter tube adjacent the distal end of the first catheter tube, and the distal waist being coupled directly to the first distal tube adjacent to a distal end of the first distal tube;
a stent positioned about at least a portion of the balloon, wherein the second distal tube is configured to exit through a side opening in the stent; and
a bond material configured to form a bond between the proximal end region of the second distal tube and an intermediate region of the first catheter tube, wherein the proximal open end of the second distal tube remains open to define a second guidewire exit port, wherein the second distal tube is bonded only to the first catheter tube and is bonded to the first catheter tube only at the bond, and wherein the bond is spaced from the proximal end of the balloon by around 10 cm to 100 cm, wherein the position of a first guidewire exit port is spaced longitudinally from the second guidewire exit port.

17. The catheter of claim 16, wherein the first guidewire exit port is positioned between 10 cm and 50 cm from the distal end of the catheter.

* * * * *

UNITED STATES PATENT AND TRADEMARK OFFICE
CERTIFICATE OF CORRECTION

| | | |
|---|---|---|
| PATENT NO. | : 8,617,231 B2 | Page 1 of 1 |
| APPLICATION NO. | : 10/670168 | |
| DATED | : December 31, 2013 | |
| INVENTOR(S) | : Gil M. Vardi | |

It is certified that error appears in the above-identified patent and that said Letters Patent is hereby corrected as shown below:

In the Specification

Column 1
Line 35: delete "currant" and insert therefor --current--.

Column 4
Line 45: delete "cain" and insert therefor --can--.

Column 6
Line 3: delete "En" and insert therefor --can--.

Column 7
Line 54: delete "fitter" and insert therefor --further--.

Signed and Sealed this
Third Day of June, 2014

Michelle K. Lee
*Deputy Director of the United States Patent and Trademark Office*